United States Patent
Glickman et al.

(10) Patent No.: US 8,957,071 B2
(45) Date of Patent: Feb. 17, 2015

(54) TREATMENT OF VASCULAR, AUTOIMMUNE AND INFLAMMATORY DISEASES USING LOW DOSAGES OF IMPDH INHIBITORS

(75) Inventors: Richard Glickman, Sidney (CA); Michael R. Hayden, Vancouver (CA); Noel Hall, Victoria (CA)

(73) Assignees: Aspreva Pharmaceuticals S.A., Neuchatel (CH); Aspreva Pharmaceuticals Corp., Victoria, British Columbia (CA)

( * ) Notice: Subject to any disclaimer, the term of this patent is extended or adjusted under 35 U.S.C. 154(b) by 1327 days.

(21) Appl. No.: 12/115,464

(22) Filed: May 5, 2008

(65) Prior Publication Data
US 2009/0088427 A1  Apr. 2, 2009

Related U.S. Application Data

(62) Division of application No. 11/351,223, filed on Feb. 8, 2006, now abandoned.

(60) Provisional application No. 60/651,452, filed on Feb. 8, 2005.

(51) Int. Cl.
*A61K 31/535* (2006.01)
*A61K 31/365* (2006.01)
*A61K 31/343* (2006.01)
*A61K 31/5377* (2006.01)

(52) U.S. Cl.
CPC .............. *A61K 31/365* (2013.01); *A61K 31/343* (2013.01); *A61K 31/5377* (2013.01)
USPC ........................................................ 514/232.5

(58) Field of Classification Search
CPC ..................................................... A61K 31/343
USPC ......................................................... 514/232.5
See application file for complete search history.

(56) References Cited

U.S. PATENT DOCUMENTS

| | | |
|---|---|---|
| 4,748,173 A | 5/1988 | Nelson et al. |
| 4,753,935 A | 6/1988 | Nelson et al. |

(Continued)

FOREIGN PATENT DOCUMENTS

| | | |
|---|---|---|
| EP | 0281713 A1 | 9/1988 |
| WO | WO 94/01105 A1 | 1/1994 |

(Continued)

OTHER PUBLICATIONS

Kingdon et al (Lupus, Sep. 2001 vol. 10 No. 9 606-611).*

(Continued)

*Primary Examiner* — Benjamin Packard
(74) *Attorney, Agent, or Firm* — COH IP Law

(57) ABSTRACT

The disclosure provides methods and compositions for treating a vascular, autoimmune, and/or inflammatory disease, or a condition associated therewith, with a dose of an inosine monophosphate dehydrogenase (IMPDH) inhibitor effective to treat the vascular, autoimmune and/or inflammatory disease, or associated condition but that does not produce immunosuppression sufficient to reduce the risk of allograft rejection. These lower doses of the immunosuppressant avoid the adverse consequences of severe immunosuppression while providing effective treatment of the vascular, autoimmune and/or inflammatory disease.

18 Claims, 5 Drawing Sheets

(56) References Cited

U.S. PATENT DOCUMENTS

| | | | |
|---|---|---|---|
| 4,808,592 A | | 2/1989 | Nelson et al. |
| 4,861,776 A | | 8/1989 | Nelson et al. |
| 4,948,793 A | | 8/1990 | Allison et al. |
| 4,952,579 A | | 8/1990 | Nelson et al. |
| 5,283,257 A | * | 2/1994 | Gregory et al. ............... 514/458 |
| 5,543,408 A | | 8/1996 | Fu et al. |
| 5,646,160 A | | 7/1997 | Morris et al. |
| 6,025,391 A | | 2/2000 | Haeberlin et al. |
| 6,043,365 A | * | 3/2000 | McQuire et al. ............... 544/280 |
| 6,172,107 B1 | | 1/2001 | Haeberlin et al. |
| 6,306,900 B1 | | 10/2001 | Haeberlin et al. |
| 6,471,980 B2 | | 10/2002 | Sirhan et al. |
| 6,541,496 B1 | | 4/2003 | Armistead et al. |
| 6,858,221 B2 | | 2/2005 | Sirhan et al. |
| 2002/0143176 A1 | | 10/2002 | Liu et al. |
| 2005/0013859 A1 | | 1/2005 | Dederichs et al. |
| 2005/0019404 A1 | | 1/2005 | Sung et al. |
| 2005/0158360 A1 | | 7/2005 | Falotico et al. |
| 2005/0250840 A1 | | 11/2005 | Moorthy et al. |
| 2005/0282876 A1 | | 12/2005 | Armistead et al. |
| 2006/0235070 A1 | | 10/2006 | Hayden et al. |
| 2008/0280932 A1 | | 11/2008 | Hayden et al. |

FOREIGN PATENT DOCUMENTS

| | | |
|---|---|---|
| WO | WO 94/12184 A1 | 6/1994 |
| WO | WO 97/38689 A1 | 10/1997 |
| WO | WO 03/032978 A1 | 4/2003 |
| WO | WO 2004/087174 A1 | 10/2004 |
| WO | WO 2004/098587 A1 | 11/2004 |
| WO | WO 2005/034916 A1 | 4/2005 |
| WO | WO 2006/024479 A1 | 3/2006 |
| WO | WO 2006/086500 A2 | 8/2006 |
| WO | WO 2008/022284 A2 | 2/2008 |

OTHER PUBLICATIONS

2005, "Effects of mycophenolate mofetil (MMF) on surrogate markers for cardiovascular disease in HIV-1 infected patients," *Clinical Trial Information*, http://www.clinicaltrials.gov/ct/show/NCT00247494 downloaded Feb. 2, 2006.

Ahrens, N. et al., Aug. 2001, "Mycophenolate-mofetil in the treatment of refractory multiple sclerosis," *J Neurol.* 248(8):713-4.

Bardsley-Elliott, A. et al., 1999, "Mycophenolate mofetil: A review of its use in the management of solid organ transplantation," *BioDrugs* 12(5):363-410.

Barilla-Labarca et al., 2003, *Curr Opin. Rheumatol.* 15(1):55-60.

Brunt et al., 2004, "Histological Changes After the Use of Mycophenolate Mofetil in Autoimmune Hepatitis," *Human Pathology* 35(4):509-512.

Buratti, S. et al., 2001, "Mycophenolate mofetil treatment of severe renal disease in pediatric onset sytemic lupus erythematosus," *J. Rheumatol.* 28(9):2103-2108.

Carroll, 2004, *Nat. Rev. Immunol.* 4(10):825-31.

Dooley, M. A. et al., 1999, "Mycophenolate mofetil therapy in lupus nephritis: clinical observations," *J. Am. Soc. Nephrol.* 10(4):833-839.

Esdaile, J. M. et al., 2001, "Traditional Framingham Risk Factors Fail to Fully Account for Accelerated Atherosclerosis in Systemic Lupus Erythematosus," *Arth. & Rheum.* 44(10):2331-2337.

Filler, G. et al., 2003, "Pharmacokinetics of mycophenolate mofetil for autoimmune disease in children," *Pediatric Nephrol.* 18(5):445-9.

Frohman, E. M. et al., 2004, "Mycophenolate mofetil in multiple sclerosis," *Clin Neuropharmacol.* 27(2):80-83.

Gaubitz, M. et al., 1999, "Mycophenolate mofetil for the treatment of systemic lupus erythrematosus: an open pilot trial," *Lupus* 8(9):731-6.

Gibson, W. T. et al., 2007, "Mycophenolate Mofetil and Atherosclerosis," *Ann. N.Y. Acad.* 1110:209-221.

International Search Report for PCT/US2006/004482 mailed Aug. 11, 2006.

International Search Report for PCT/US2006/004484 mailed Aug. 3, 2006.

Kamiyoshi, Y. et al., 2005, "Mycophenolate mofetil prevents the development of experimental autoimmune myocarditis," *J. Mol. Cell Cardiol.* 39:467-477.

Karim, M. Y., 2002, "Mycophenolate mofetil for systemic lupus erythematosus refractory to otherimmunosuppressive agents," *Rheumatology* (Oxford). Aug. 2002;41(8):876-82.

Kingdon, E. J., 2001, "The safety and efficacy of MMF in lupus nephritis: a pilot study, "*Lupus* 10(9):606-11.

Li, L. et al., 2002, "Mycophenolate mofetil treatment for diffuse proliferative lupus nephritis: a multicenter clinical trial in China," *Chin J. Intern Med.* 41(7):476-9.

Maksimovic-Ivanic, D. et al., 2002, "Down-regulation of multiple low dose streptozotocin-induced diabetes by mycophenolate mofetil," *Clin. Exp. Immunol.* 129(2):214-223.

Miller, L. W., 2002, "Cardiovascular toxicities of immunosuppressive agents," *Am. J. Transplant* 2(9):807-818.

Moder, K. G., 2003, "Mycophenolate mofetil: new applications for this immunosuppressant," *Ann Allergy Asthma Immunol.* 90(1):15-19.

Neumann, I. et al., 2003, "Pharmacokinetics of mycophenolate mofetil in patients with autoimmune diseases compared renal transplant recipients," *J Am Soc Nephrol.* 4(3):721-727.

Ramos, M. A. et al., 2002, "Modulation of autoantibody production by mycophenolate mofetil: effects on the development of SLE in (NZB × NZX)F1 mice," *Nephrol. Dial. Transplant* 18(5):878-883.

Romero, F. et al., 2000, "Mycophenolate mofetil treatment reduces cholesterol-induced atherosclerosis in the rabbit," *Atherosclerosis* 152(1):127-133.

Ross, R., 1999, "Atherosclerosis—an inflammatory disease," *N. Engl. J Med.* 340:115-126.

Schneider, C. et al., 2002, "Mycophenolate mofetil in the therapy of polymyositis associated with a polyautoimmune syndrome," *Muscle Nerve*, 25(2):286-288.

Shimizu, H. et al., 2004, "Mycophenolate mofetil prevents transplant arteriosclerosis by direct inhibition of vascular smooth muscle cell proliferation.," *Transplantation* 77(11):1661-1667.

Van Leuven, S. I. et al., 2006, "Mycophenolate mofetil (MMF):Firing at the atherosclerotic plaque from different angles?" *Cardiovasc. Res.* 69(2):341-7.

U.S. Appl. No. 12/377,384 Hayden et al.

U.S. Appl. No. 13/080,619 entitled "Compositions and Methods for Treating Vascular, Autoimmune, and Inflammatory Diseases," filed on Apr. 5, 2011.

U.S. Appl. No. 12/964,722 entitled "Compositions and Methods for Treating Vascular, Autoimmune, and Inflammatory Diseases", filed Dec. 9, 2010.

Beers and Berkow, *The Merck Manual of Diagnosis and Therapy*, Chapter 15, p. 200-202 and 207-209, Merck Research Laboratories (1999).

European Search Report for European Patent Application No. EP07814181, dated Aug. 12, 2011.

International Preliminary Examination Report and Written Opinion for PCT/US2006/004482 dated Aug. 14, 2007.

International Preliminary Examination Report and Written Opinion for PCT/US2006/004484 dated Aug. 14, 2007.

Physicians' Desk Reference, 59th Ed.. Thompson PDR, Montvale, NJ, pp. 2855, 2861 (2005).

* cited by examiner

TREATMENT OF VASCULAR, AUTOIMMUNE AND INFLAMMATORY DISEASES USING LOW DOSAGES OF IMPDH INHIBITORS

CROSS REFERENCE TO RELATED APPLICATIONS

This application is a division of application Ser. No. 11/351,223, filed Feb. 8, 2006, which claims benefit under 35 U.S.C. §119(e) to application Ser. No. 60/651,452, filed Feb. 8, 2005, the contents of which are incorporated herein by reference.

FIELD

The present disclosure relates generally to compositions and methods for treating vascular, autoimmune and inflammatory diseases, and conditions associated with such diseases, by administering to subjects low dosages of drug compounds that inhibit inosine monophosphate dehydrogenase, and/or prodrugs of such compounds.

BACKGROUND

Inosine monophosphate dehydrogenase (IMPDH) is the rate-limiting enzyme in the de novo biosynthesis of guanosine nucleotides in mammals. Both T- and B-lymphocytes rely exclusively on de novo guanosine nucleotide synthesis, as they are deficient in salvage pathways.

Mycophenolic acid ("MPA") is a potent inhibitor of IMPDH that has gained widespread acceptance as an immunosuppressant, particularly in the prophylactic treatment of organ rejection in patients receiving allogenic renal, cardiac or hepatic transplants. MPA treatment in the form of the 2-morpholinoethyl ester prodrug mycophenolate mofetil ("MMF"; structure illustrated below) is marketed in the U.S. for these indications by Hoffman LaRoche under the tradename CellCept®:

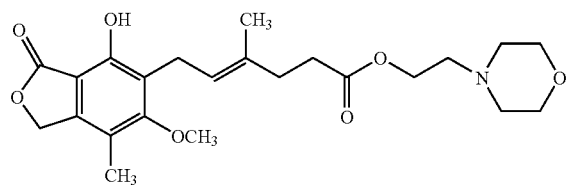 [SMILES: COc1c(C)c2c(c(O)c1C/C=C(\C)CCC(=O)OCCN1CCOCC1)C(=O)OC2]

CellCept® is currently available in capsule (250 mg), tablet (250 mg and 500 mg), oral suspension (200 mg/ml when constituted), and intravenous (6 mg/ml in 5% dextrose when reconstituted) dosage forms. Following oral or intravenous administration, the MMF is rapidly and completely metabolized to the active metabolite MPA (see, e.g., Physicians Desk Reference, 2005 Ed., pp. 2855; "PDR").

A delayed-release, enterically coated tablet formulation of the sodium salt of mycophenolic acid (mycophenolate sodium) is marketed in the U.S. by Novartis AG under the tradename Myfortic®. Each tablet contains either 180 mg or 360 mg of mycophenolate sodium. According to the 2005 Edition of the PDR, Myfortic® is currently approved for the prophylactic treatment of organ rejection in patients receiving allogenic renal transplants.

The recommended dose of CellCept® is 1 g administered orally or intravenously twice daily for renal transplant (i.e., a daily dose of 2 g; corresponding to a daily dose in the range of about 20-45 mg/kg for a patient body mass in the range of 45-100 kg) and 1.5 g administered orally or intravenously twice daily for hepatic and cardiac transplant (i.e., a daily dose of 3 g; corresponding to a daily dose of about 30-67 mg/kg for a patient body mass in the range of 45-100 kg). The recommended dose of Myfortic® is 720 mg administered orally twice daily (i.e., a daily dose of 1.44 g; corresponding to a daily dose in the range of about 14 mg/kg-32 mg/kg for a patient body mass in the range of 45-100 kg). These relatively large doses are required because clinical evidence does not support their effectiveness to prevent transplant rejection at lower doses. These standard doses require that tablets be of inordinate size so that a patient may consume a minimum number. For MMF, the minimum size tablet approved is 250 mg, with 500 mg being the commonly prescribed tablet. For MPA, the minimum size tablet approved is 180 mg.

Efforts to identify other indications for MMF and MPA have met with limited success to date. Treatment of diabetic nephropathy employing a combination therapy of an ACE inhibitor (Lisinopril; S-1-[$N^2$-(1-carboxy-3-phenylpropyl)-L-lysyl]-L-proline dehydrate) and MMF at a dose of 1 g/day (10-22 mg/kg/day depending on patient body mass) has been proposed (PCT publication WO 04/98587). Romero et al., 2000, *Atherosclerosis* 152:127-133, provided evidence that MMF administered to rabbits at 30 mg/kg/day ameliorated the atherogenic potential of a high-cholesterol diet. This work followed Schreiber et al., 1998, *Transpl. Proc.* 30:901-902, which studied the effect of MMF at 80 mg/kg (subcutaneous injection) in a similar model. Neither of these indications have received approval from regulatory agencies.

A need exists to identify improved therapeutic compositions and methods that can be used for the therapeutic and/or prophylactic treatment of vascular, autoimmune, and/or inflammatory diseases. The instant disclosure provides such compositions and methods, relying on a novel understanding of IMPDH inhibitors and their utility in treating certain vascular, autoimmune and/or inflammatory disease processes.

SUMMARY

In one aspect, the present disclosure provides methods for treating vascular, autoimmune and/or inflammatory diseases, and conditions associated with such diseases, in subjects by administering IMPDH inhibitory compounds and/or prodrugs of such IMPDH inhibitory compounds (including the corresponding salts, hydrates and solvates thereof). The amount of compound administered will depend upon the specific identity of the compound, but will generally be less than the amount that would be administered to prophylactically treat allograft transplant rejection (for example, renal, hepatic, or cardiac transplant rejection). In some embodiments, the amount of compound administered is a low dose, an extra-low dose or an ultra-low dose of the compound and/or prodrug, as will be described further hereinbelow.

The compound administered can be any compound that inhibits the activity of IMPDH, or a prodrug of such an IMPDH-inhibitory compound (i.e., a compound that metabolizes under conditions of use to a compound that inhibits the activity of IMPDH). Such IMPDH inhibitory compounds and prodrugs are well-known, and include by way of example and not limitation, inhibitors 3-(1-deoxy-beta-D-ribofuranosyl) benzamide (Jayaramet et al., 1992, *Biochem Biophys Res Commun.* 186(3):1600-6); mizoribine, 5-beta-D-ribofuranosylselenophene-3-carboxamide (Franchetti et al., 1997, *J Med Chem.* 40(11):1731-7); N-[2-[2-[[3-methoxy-4-(5-oxazolyl)phenyl]amino]-5-oxazolyl]phenyl]-N-methyl-4-morpholineacetamide (Dhar et al., 2002, *J Med Chem.* May 45(11):2127-30), and mycophenolic acid (MPA) and their various corresponding salts, hydrates, solvates and esters. Other IMPDH inhibitors include compounds disclosed in U.S. Pat. Nos. 5,807,876; 5,932,600; 6,054,472; 6,344,465; 6,420,403; 6,518,291; 6,541,496; 6,596,747; 6,617,323; and 6,624,184. In some embodiments, the IMPDH inhibitory compound administered is mycophenolic acid and/or a salt, hydrate, solvate and/or ester thereof. In a specific embodiment, the compound administered is selected from a salt of mycophenolic acid, such as, for example, mycophenolate sodium, and an ester of mycophenolic acid, such as, for example, mycophenolate mofetil (MMF).

The methods may be practiced therapeutically in patients suffering from a vascular, autoimmune and/or inflammatory disease, or a condition associated therewith. In some embodiments, the inhibitory compound can be administered prophylactically in patients that do not currently suffer from such a disease or condition. Thus, in some embodiment, the prophylactic therapy is administered to patients who are at risk of developing a vascular, autoimmune and/or inflammatory disease or a condition associated with a vascular, autoimmune and/or inflammatory disease.

In some embodiments, the condition treated is associated with an autoimmune disease, such as systemic lupus erythematosus (SLE), rheumatoid arthritis, and diabetes mellitus, and includes conditions such as atherosclerosis, cardiovascular disease, and other vascular diseases, which occur at higher frequency in such patients. In other embodiments, the condition associated with the autoimmune disease is an inflammatory reaction, which typically accompanies many different autoimmune reactions. In various embodiments, the IMPDH inhibitory compounds may be administered at doses effective to treat or reduce the risk of developing the associated condition regardless of the effectiveness of the drugs on the underlying disease.

In another aspect, the present disclosure provides pharmaceutical compositions comprising an IMPDH inhibitory compound, and/or a prodrug of such a compound (including salts, hydrates and/or solvates of such compounds and prodrugs) and one or more pharmaceutically acceptable carriers, excipients and/or diluents. The amount of compound and/or prodrug included in the composition is specifically suited to provide therapeutic and/or prophylactic benefit in the methods described herein. Accordingly, in some embodiments, the compositions will generally comprise unit dosage amounts or fractional unit dosage amounts of IMPDH inhibitory compounds and/or prodrugs that are tailored to administer low, extra-low or ultra-low daily dosages of the compounds and/or prodrugs. Non-limiting examples of IMPDH inhibitory compounds and prodrugs that can be included in the pharmaceutical compositions are those provided above.

The pharmaceutical compositions can be suited for virtually any mode of administration, including, but not limited to, oral and intravenous administration. In some embodiments, the pharmaceutical compositions are oral tablets or capsules. In one specific embodiment, the tablets or capsules comprise a salt of mycophenolic acid, such as, for example, mycophenolate sodium, and/or an ester of mycophenolic acid, such as, for example, mycophenolate mofetil, and one or more excipients. In a specific embodiment, the total amount of mycophenolate salt and/or mycophenolate ester comprising the tablets or capsules is selected from one, one-half, one-third and one-fourth of the amount necessary to achieve a low, an extra-low or an ultra-low daily dose.

DETAILED DESCRIPTION

Figure 1:
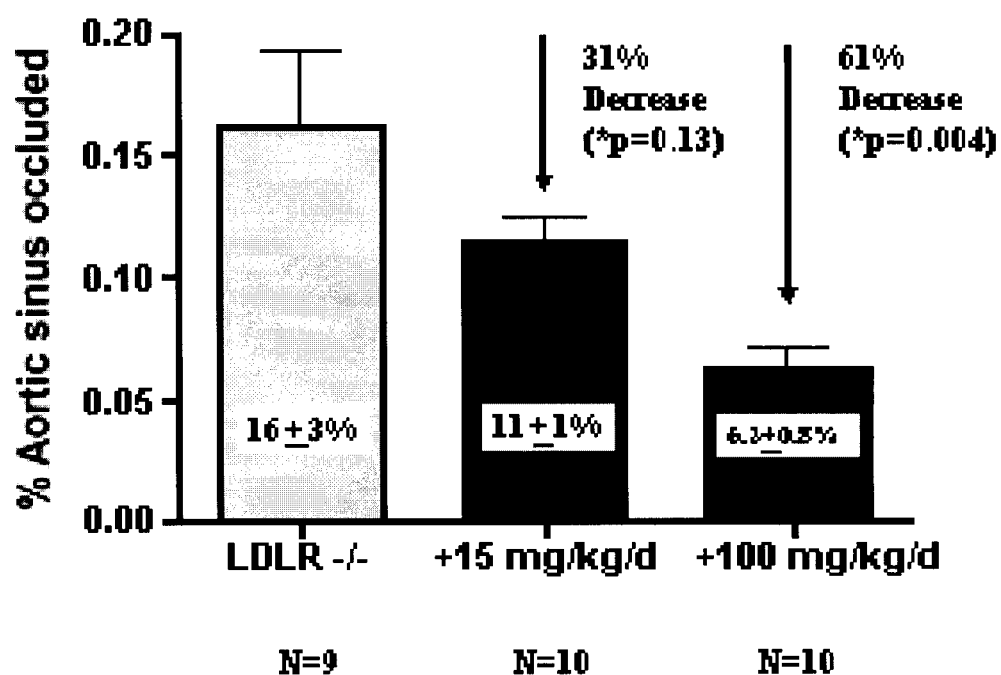
FIG. 1 illustrates the effect of administering mycophenolate mofetil to Ldlr –/– mice at a dosage of 15 mg/kg/day in reducing atherosclerotic plaques.

As discussed in the Summary, IMPDH inhibitory compounds and prodrugs, such as MPA and MMF, have gained widespread success in preventing or reducing the risk of rejection in patients receiving allogenic organ transplants. The standard dosages administered in this context range from 1.44 to 3 g daily. The methods described herein, however, relate to the use of lower doses of these agents for the treatment and/or prevention of indications not previously indicated for IMPDH inhibitors, such as for example, vascular, autoimmune and inflammatory diseases, and conditions associated with vascular, autoimmune and inflammatory diseases.

While not intending to be bound or limited by any theory of operation, the methods and compositions described herein are based, in part, on the inventors' recognition that the anti-inflammatory action of IMPDH inhibitory compounds and prodrugs (for example, MPA and MMF), will provide therapeutic and/or prophylactic benefit for diseases that involve, at least in part, an immune inflammatory response when the compounds and/or prodrugs are administered at dosages that produce only modest immunosuppression in the patient, rather than the comprehensive immunosuppression resulting from the standard doses necessary to reduce the risk of allogenic transplant rejection.

From studies of patients afflicted with systemic lupus erythematosus (SLE), an autoimmune disease with an associated inflammatory component, the inventors recognize that the risk of myocardial infarction is increased by as much as 9-fold in patients with SLE, even after adjustment for CVD risk factors such as hypertension and high cholesterol (see, Esdaile et al., 2001, *Arth. & Rheum.* 44(10):2331-2337). Unstable, rupture prone plaques, which are thought to be responsible for incidences of myocardial infarction and other ischemic events, have identifiable features, including numerous inflammatory cells. These unstable plaques are characterized by active inflammation that may overwhelm the plaque's capacity for repair (Ross, 1999, "Atherosclerosis—An Inflammatory Disease," *N Engl J Med.* 340:115-126). Macrophages and T cells are abundant in the regions of plaque rupture, while smooth muscle cells are few. Conversely, stable plaques contain few inflammatory cells, and have abundant smooth muscle cells. Thus, a defective inflammatory response involved in SLE may be responsible for the underlying disease and also the cardiovascular outcomes of the disorder.

On the other hand, clinical and genetic studies in humans and animal models indicate a crucial protective role for the complement system in systemic lupus erythematosus (SLE). This presents a paradox, because the complement system is considered to be an important mediator of the inflammation that is observed in patients with SLE. One current view is that complement provides protection by facilitating the rapid removal of apoptotic debris to circumvent an autoimmune response (Barilla-LaBarca et al., 2003, *Curr Opin Rheumatol.* 15(1):55-60). In an alternative model, complement, together with other components of the innate immune system, participates in the "presentation" of SLE-inducing self-antigens to developing B cells. In this way, the complement system and innate immunity may protect against responses to SLE (self) antigens by enhancing the elimination of self-reactive lymphocytes (see, Carroll, 2004, *Nat Rev Immunol.* 4(10):825-31).

Because the inflammatory component and the self reactive lymphocytes prominent in SLE may be responsible for the adverse physiological effects seen in patients afflicted with SLE, immunosuppressive therapy with IMPDH inhibitors and/or prodrugs of such inhibitors at levels sufficient to reduce the inflammatory reaction and attenuate the activity of self-reactive lymphocytes may provide a therapeutic benefit to such patients. This effect may be achieved at doses below those required to reduce the risk of allograft rejection, thus avoiding the harsh consequences of severe immunosuppression.

Furthermore, since other autoimmune diseases and inflammatory conditions arise from dysregulation of the immune system similar to that observed in SLE, the methods disclosed herein may be applicable to these diseases as well. Examples of such diseases include, but are not limited to vascular, autoimmune and inflammatory diseases.

As such, in various embodiments, the IMPDH inhibitory compounds can be used to treat patients who manifest clinical indications of the disease. In some embodiments, the compositions and methods are used to treat vascular diseases that include, by way of example and not limitation, atherosclerosis, coronary heart disease (CHD), cardiovascular disease (CVD), coronary artery disease (CAD), cerebrovascular disease, and peripheral vascular disease.

In other embodiments, the compositions and methods are used to treat autoimmune diseases that include, by way of example and not limitation, systemic lupus erythematosus (SLE), multiple sclerosis (MS), diabetes mellitus, and rheumatoid arthritis (RA).

In still other embodiments, the compositions and methods are used to treat inflammatory diseases that include, by way of example and not limitation, Crohn's disease, ulcerative colitis, pelvic inflammation, and vasculitis. An exemplary inflammatory disease treatable with the compositions is vasculitis, a condition arising from inflammation of the blood vessel system, which includes the veins, arteries, and capillaries. Vasculitis may affect blood vessels of any type, size, or location, and therefore can cause dysfunction in any organ system, including the central and peripheral nervous systems.

In some embodiments, the compositions and methods herein are used to treat or reduce the risk of a condition associated with a vascular, autoimmune or inflammatory disease. In these embodiments, doses of the IMPDH inhibitor can be administered for treatment of the associated condition regardless of whether the underlying disease is treated. For example, as noted above, the autoimmune disease SLE is associated with increased atherosclerosis and cardiovascular disease such that they constitute one of the leading causes of death in SLE patients. The risk of myocardial infarction increases by as much as 9 fold in patients with SLE. Hence, the compositions disclosed herein can be administered to treat or reduce the risk of atherosclerosis and cardiovascular disease associated with SLE, regardless of whether the doses are effective in treating the SLE. Other autoimmune diseases manifesting an increased vascular disease occurrence include, among others, diabetes mellitus (i.e., type I diabetes) and rheumatoid arthritis. Thus, in some embodiments, the compositions can be used in a method to treat or reduce the risk of atherosclerosis, cardiovascular disease, or other vascular diseases in a subject with a pre-existing autoimmune disease, such as, for example, SLE, diabetes mellitus, and rheumatoid arthritis.

In some embodiments, the associated condition is an inflammatory condition associated with autoimmune disease. For example, chronic inflammation accompanies many forms of autoimmune disease, such as rheumatoid arthritis, systemic lupus, and diabetes mellitus. The inflammatory cascade activated by the autoimmune reaction can exacerbate the damage caused by the autoimmune reaction. In some cases, a patient with an underlying autoimmune disease may not display clinical signs of an inflammatory reaction, but have levels of biochemical markers indicative of inflammatory reactions (e.g., inflammatory cytokine levels). As such, the compositions and methods herein can be used to treat or reduce the risk of such inflammatory conditions associated with autoimmune diseases. Thus, in some embodiments, the compositions can be used in a method to treat or reduce the risk of inflammatory reactions in a subject with a pre-existing autoimmune disease.

In some embodiments, the compositions can be used in methods to lower serum triglyceride levels. The studies herein indicate that MMF can lower triglyceride levels in a mouse model of atherosclerosis. In some embodiments, the elevated triglyceride level may be a condition associated with a pre-existing disease or be present in an otherwise healthy subject, as further described below.

In some embodiments, the subjects treated are healthy but have an increased risk or susceptibility to the diseases or associated conditions. In some embodiments, the subjects may have a genetic predisposition to the disease, as indicated by family history or genetic testing. In other embodiments, the subject may display one or more indications associated with an increased risk or susceptibility to the disease. Exemplary embodiments of markers for increased risk of vascular disease include, among others, obesity, low HDL level, elevated cholesterol level, high fasting glucose, elevated blood pressure, and elevated levels of C-reactive protein, serum amyloid A, homocysteine, and inflammatory cytokines (e.g., interleukin-6, tumor necrosis factor-alpha, interleukin-8, etc.). Exemplary embodiments of markers for increased risk of autoimmune disease include, among others, presence of immuno-reactive autoantibodies and corresponding autoantigens (see, e.g., Lernmark, A., 2001, *J Clin Invest.* 108:1091-1096), and an MHC type associated with autoimmune diseases (see, e.g., Weyand and Goronzy, 2000, *Arthritis Res.* 2(3):203-4).

In various embodiments, the compositions and methods herein are directed to adult subjects. As used herein, "adult" in the context of human subjects refers to a person of about 18 years or older. As further described below, in some embodiments, the dosages administered are less than the dosages required to suppress the immune system for reducing the risk of organ rejection in an adult transplant patient. In some embodiments, the adult subjects may be further grouped into various age groups for purposes of treatment. For example, it is understood that as a human ages, there is an increased incidence of certain diseases that are "age related," such as atherosclerosis, cardiovascular disease, arthritis, rheumatoid arthritis, and type II diabetes. Thus, older age groups can benefit from therapy with the IMPDH inhibitors as compared to subjects in younger age groups. Grouping of adult subjects may also be useful for taking into consideration differences in metabolism of the IMPDH inhibitory compounds by different age groups. Thus, in some embodiments, treatments with IMPDH inhibitors can be directed to those in the group of about 65 years or older, in the group of about 50 to about 64 years of age, in the group of about 40 to about 49 years of age, and in the group of about 18 years to about 39 years of age. In some embodiments, the low-dose, extra-low dose, or ultra-low doses can be used to delay the onset of such disease or lessen its severity in older patient populations that are at increased risk for such age related diseases, such as, for example, patients who are 50 years or older.

In other embodiments, the treatments are directed to children and adolescents younger than 18 years old, of about 12 years old or younger, of about 6 years old or younger, or of about 4 years old or younger. Dosages of MMF and MPA typically administered to pediatric transplant patients are about 1.5 gm/day. Thus, in some embodiments, the low-dose, extra-low dose, or ultra-low dose may be administered to children and adolescents diagnosed with or at increased risk for vascular, autoimmune, and/or inflammatory diseases, and conditions associated therewith. For example, nearly a quarter of all systemic lupus cases are diagnosed in children. Thus, MMF and MPA can be administered to these pediatric patients for ameliorating the SLE and/or reducing the risk of conditions associated with SLE, such as cardiovascular disease and atherosclerosis, that may begin early in life for pediatric patients with SLE.

In the methods described herein, subjects are administered dosages of IMPDH inhibitory compounds that are lower than the standard dosages typically administered to reduce the risk of allograft rejection. As discussed in the Summary, above, a "standard dose" of MMF or MPA for the prevention of allograft organ rejection ranges from about 1.44 to 3.0 g/day. At lower dosages, therapeutic and/or prophylactic benefit can be achieved while avoiding or minimizing the adverse consequences of severe immunosuppression achieved with standard doses of such compounds The actual dosages administered will depend upon the particular indication being treated, and other factors such as the weight of the patient, the overall health of the patient, and other factors that will be apparent to the prescribing physician. In some embodiments, the subject is administered a "low," an "extra-low," or an "ultra-low" dose of an IMPDH inhibitory compound.

As used herein, "IMPDH inhibitory compound" or "IMPDH inhibitor" refers to any compound that inhibits or reduces the activity of inosine monophosphate dehydrogenase (IMPDH), the rate-limiting enzyme in the de novo biosynthesis of guanosine nucleotides. Also included within the definition are prodrugs of such IMPDH inhibitory compounds (for example, esters of such compounds) that metabolize under their conditions of use to an active metabolite that is an IMPDH inhibitory compound. Significant members of the class of IMPDH inhibitory compounds are mycophenolic acid ("MPA") and its corresponding salts, hydrates, solvates and esters, and mycophenolate mofetil ("MMF") and its corresponding salts, hydrates and solvates. Specific embodiments of salts and analogs of MMF, as well as methods of making the salts and analogs, are described in U.S. Pat. Nos. 4,686,234; 4,725,622; 4,727,069; 4,748,173; 4,753,935; 4,786,637; 4,808,592; 4,861,776; 4,868,153; 4,948,793; 4,952,579; 4,959,387; and 4,922,467; the disclosures of which are incorporated herein by reference. Additional exemplary IMPDH inhibitory compounds, as well as methods for their synthesis, include, but are not limited to, 3-(1-deoxy-beta-D-ribofuranosyl)benzamide (Jayaram et al., 1992, *Biochem Biophys Res Commun.* 186(3):1600-6); mizoribine, 5-beta-D-ribofuranosylselenophene-3-carboxamide (Franchetti et al., 1997, *J Med Chem.* 40(11):1731-7); and N-[2-[2-[[3-methoxy-4-(5-oxazolyl)phenyl]amino]-5-oxazolyl]phenyl]-N-methyl-4-morpholineacetamide (Dhar et al., 2002, *J Med Chem.* May 45(11):2127-30), the disclosures of which are incorporated herein by reference.

MMF is the 2-morpholinoethyl ester prodrug of MPA. When administered orally or intravenously, MMF rapidly and completely metabolizes to MPA. MPA is a selective, non-competitive and reversible inhibitor of IMPDH (in particular the type II isoform) and strongly inhibits both T- and B lymphocyte proliferation. MMF has been used in the prevention of acute and chronic allograft rejection since the mid 1990s under the trade name CellCept® (F. Hoffman-La Roche, AG). An enterically coated formulation of the sodium salt of MPA (mycophenolate sodium) has been approved for prophylaxis of rejection in allogenic renal transplants under the tradename Myfortic® (Novartis AG).

As used herein, a "low dose" of MMF or MPA is less than 2.0 g/day. In some embodiments, a "low dose" of MMF or MPA ranges from about 0.5 to 1.75 g/day (e.g., 0.5, 0.75, 1.0, 1.25, 1.5 and 1.75 g/day). These doses correspond to 5-39 mg/kg/day, depending on patient body mass, including 5 to 11, 5 to 17, 5 to 22, 5 to 28, and 5 to 33 mg/kg/day. In some embodiments, a "low dose" of MMF or MPA is about 5, 6, 7, 8, 9, 10, 11, 12, 13, 14, 15, 16, 17, 18, 19, 20, 21, 22, 23, 24, 25, 26, 27, 28, 29, or 30 mg/kg/day. In other embodiments, a low dose is in the range of about 10-15 mg/kg/day.

An "extra-low dose" of MMF or MPA is 1.0 g/day or less. In some embodiments, an "extra-low dose" of MMF or MPA ranges from about 100 to 500 mg/day (e.g., 100, 125, 150, 175, 200, 225, 250, 300, 350, 400 and 500 mg/day). These doses correspond to about 1 to 11 mg/kg/day, depending on patient body mass, including 1 to 2, 1 to 3, 1 to 4, 1 to 5, 1 to 6, 1 to 7, 1 to 8, 1 to 9, and 1 to 10 mg/kg/day. In some embodiments, an extra-low dose is about 1, 2, 3, 4, or 5 mg/kg/day.

An "ultra-low dose" of MMF or MPA is 0.5 g/day or less. In some embodiments, an "ultra-low dose" of MMF or MPA ranges from about 5 to 100 mg/day, (e.g., 5, 10, 20, 25, 30, 40, 50, 60, 70, 75, 80, 90, and 100 mg/day). These doses correspond to about 0.05 to 2.2 mg/kg/day, depending on patient body mass, including 0.05 to 0.10, 0.05 to 0.20, 0.05 to 0.30, 0.05 to 0.50, 0.05 to 0.70, 0.05 to 0.90, 0.05 to 1.10, 0.05 to 1.30, 0.05 to 1.50, 0.05 to 1.80, and 0.05 to 2.00 mg/kg/day. In some embodiments, an ultra-low dose is about 0.1, 0.2, 0.3, 0.4, 0.5, 0.6, 0.7, 0.8, 0.9, or 1.0 mg/kg/day.

The IMPDH inhibitors may be administered therapeutically to subjects that are suffering from the particular indication to achieve a therapeutic benefit. As used herein, therapeutic benefit includes, in addition to treating the underlying indication, reducing and/or ameliorating the overall number and/or severity of its associated symptoms and/or halting or slowing the progression of the indication and/or its symptoms. For example, as noted above, the IMPDH inhibitors may be administered therapeutically to individuals afflicted with an indication to avoid the onset of symptoms or side-effects associated with the indication, regardless of whether the underlying the indication is treated.

Alternatively, the IMPDH inhibitors may be administered prophylactically to subjects that are not suffering from the particular indication to achieve prophylactic benefit. As described above, in some embodiments, the IMPDH inhibitors are administered prophylactically to subjects that are at a high or higher risk than the normal population of developing the particular indication.

As used herein, "subject" refers to a mammal, in particular a human, at any stage of life. Generally, subjects are patients who have not received an allograft transplant. Allograft transplant means any organ or cell transplant between individuals of the same species. Allograft transplant includes organ, tissue, bone, connective tissue, and cells used to help repair defects, eliminate or reduce pain and promote faster healing. Tissue includes bone, skin, heart valves, connective tissue and veins. Allograft organ and cell transplants include, by way of example and not limitation, the heart, lungs, kidneys, intestines, pancreas, liver, and hematopoietic stem cells. However, in some embodiments, the lower, low, extra-low and/or ultra-low doses if IMPDH inhibitory compounds disclosed herein may be used to treat subjects that have received allograft organ or cell transplants who are being treated with immunosuppressants other than IMPDH inhibitors at levels sufficient to reduce the risk of allograft rejection (i.e., severe immunosuppression). General classes of immunosuppressants include, by way of example and not limitation, glucocorticosteroids, calcineurin inhibitors, and antiproliferative/antimetabolic agents. Examples of such non-IMPDH immunosuppressants include, but are not limited to, cyclosporin, tacrolimus (FK506), prednisone, prednisolone, rapamycin, cyclophosphamide, azathioprine, OKT3 (anti-CD3 monoclonal antibody), and thymoglobulin (anti-thymocyte globulin).

The "lower," "low," "extra-low" and "ultra-low" daily doses described above may be achieved by administering the MMF or MPA in unit dosage amounts, or, alternatively, the daily doses may be achieved by administering MMF or MPA in two or more equal or unequal dosage amounts during the course of the day, such that the total amount of MMF or MPA administered per day equals the total amount desired (for example, a "lower," "low," "extra-low" or "ultra-low" daily dose).

The various daily dosages can be achieved by utilizing commercially available MMF or MPA compositions. For example, a number of commercially available 250 mg or 500 mg CellCept® tablets, or a number of commercially available Myfortic® tablets, can be taken that would yield the desired daily dosage. Where necessary or desired, the CellCept® or Myfortic® tablets can be divided into appropriately sized aliquots with the aid of a pill cutter. The amounts of commercially available capsule, oral suspension and intravenous CellCept® formulations can also be adjusted to administer "lower," "low," "extra-low" and/or "ultra-low" daily doses as described herein.

While commercially-available MMF and MPA compositions can be used, in many embodiments, it will more convenient for the patient to take compositions that have been specifically formulated to achieve "lower," "low," "extra-low" and/or "ultra-low" daily doses as described herein. Thus, the present disclosure includes compositions of IMPDH inhibitory compounds, such as MMF and MPA, that are specifically tailored to provide the lower, low, extra-low and ultra-low daily dosages described herein, either in unit dosage amount, or in a convenient number of fractional doses. The compositions may take the form of a pill, capsule or tablet, containing the desired amount of IMPDH inhibitory compound(s), although oral suspensions and intravenous or parenteral formulations are also contemplated herein.

When provided in the form of a pill, capsule or tablet, the composition may optionally comprise, along with the desired amount of IMPDH inhibitory compound, one or more excipiating agents, including, for example, a diluent such as lactose, sucrose, dicalcium phosphate, and the like; a disintegrant such as starch or derivatives thereof like pregelatinized starch (corn); a lubricant such as magnesium stearate, and the like; and a binder such as starch, gum acacia, polyvinylpyrrolidone, gelatin, cellulose and derivates thereof, and the like.

Additional non-limiting examples of optional excipiating agents that may comprise the pills, capsules and/or tablets include, among others, butylated hyrdoxyanisole NF, citric acid monohydrate USP, croscarmellose sodium NF, hydroxypropyl cellulose; hydroxypropyl methylcellulose USP, iron oxides, lactose monohydrate NF, magnesium stearate NF, potassium bicarbonate, povidone, povidone K-90, ammonium hydroxide, microcrystalline cellulose NF, Opadry White YS-1-7040, polyethylene glycol, PEG 8000, sodium lauryl sulfate, polysorbate 80 NF, simethicone emulsion, talc, titanium dioxide, calcium carbonate USP, candelilla wax FCC; FD&C Blue 2, D&C Yellow 10, ethyl alcohol, methyl alchol, n-butyl alcohol, propylene glycol, shellac and propyl gallate NF.

Non-limiting examples of excipiating agents that may be included in capsules include benzyl alcohol, black iron oxide, butylparaben, edentate calcium disodium, methylparaben, propylparaben and sodium propionate.

Compositions that are in the form of tablets may include optional coatings designed, for example, to be resistant to the acid environment of the stomach and remain undissolved until they reach the alkaline environment of the small intestine. Films that dissolve between pH 5.5 and 6.5 are generally preferred. A wide variety of such coatings are known to those skilled in the art.

Liquid pharmaceutically administrable compositions can be prepared by dissolving, dispersing, etc., the active compounds (each about 0.5% to about 40%), as described above, and optional pharmaceutical adjuvants in a carrier, such as for example, water, saline, aqueous dextrose, glycerol, ethanol and the like, to thereby form a solution or suspension. In 5% dextrose solution, MMF has a solubility of 65.8 mg/ml and a pH of 2.4 to 4.1. Inactive ingredients in liquid formulation may further include aspartame, citric acid anhydrous, colloidal silicon dioxide, mixed fruit flavor, sodium citrate dehydrate, sorbitol, soybean lecithin and xanthan gum.

If desired, the pharmaceutical composition may also contain minor amounts of non-toxic auxiliary substances such as wetting or emulsifying agents, pH buffering agents and the like, such as for example, sodium acetate, sorbitan monolaurate, triethanolamine oleate, etc.

Methods of preparing the various dosage forms discussed are known, or will be apparent, to those skilled in this art; for example, see *Remington's Pharmaceutical Sciences*, 2000, 20th edition (Mack Publishing Company, Easton, Pa.), incorporated herein by reference. The composition to be administered will, in any event, contain a quantity of the active compound in a therapeutically effective amount for relief of the particular disease or condition being treated when administered in accordance with the teachings of this disclosure.

Mycophenolate mofetil, or morpholinoethyl E-6-(1,3-dihydro-4-hydroxy-6-methoxy-7-methyl-3-oxo-5-isobenzofuranyl)-4-methyl-4-hexenoate, can be made as described in U.S. Pat. No. 4,753,935. The pharmaceutically acceptable salts or derivatives of mycophenolate mofetil can be made as described in U.S. Pat. Nos. 4,686,234; 4,725,622; 4,727,069; 4,748,173; 4,753,935; 4,786,637; 4,808,592; 4,861,776; 4,868,153; 4,948,793; 4,952,579; 4,959,387; and 4,922,467. Combination of the active ingredient and inactive ingredients into the desired pill, tablet, capsule or liquid formulation of the invention can be achieved according to known methods standard in the art.

EXAMPLES

Example 1

Effect of Low-Dose MMF on a Mouse Model of Atherosclerosis

This example illustrates the effect of low-dose MMF on mice lacking the low-density lipoprotein receptor B6.129S7-Ldlrtm1Her/J (hereinafter referred to as LDLRKO mice) obtained from Jackson Labs. When placed on a high-fat, high-cholesterol "Western-type" diet, these mice develop severe atherosclerosis (Ishibashi et al., 1994, *J Clin Invest.* 93(5):1885-93).

Study Design: Male mice will be fed a high-fat, high-cholesterol "Western-type" diet (15% cocoa butter, 0.25% cholesterol by weight, 34% of calories from fat ("Diet W" Hope Farms, Woerden, Netherlands) for 12 weeks, a time which has been shown to be sufficient for the mice to develop significant atherosclerosis, as assessed by the appearance of atheromatous lesions at the aortic root.

Studies show that male LDLRKO mice consume, on average, 3.3 grams of Diet W per mouse per day. Diet W will be formulated with CellCept® incorporated directly into the chow, at concentrations of 0.04%, 0.08% or 0.26% mycophenolate mofetil by weight. When administered in this way, the mice will be expected to consume 15 mg/kg/day ("low dose"), 30 mg/kg/day ("low dose"), or 100 mg/kg/day ("high-dose") of the drug. Mice will be sacrificed 12 weeks after feeding on the study diet, and the endpoints determined.

The primary endpoint will be evaluated using histological analysis of plaque area at the aortic root. The total lesion area in oil red O-stained cryostat sections of the aortic root is quantified using a Leica image analysis system. Mean lesion area (as a percentage of aortic cross-sectional area) is calculated from 10 oil red O-stained sections, beginning at the appearance of the tricuspid valves.

Plaque composition is analysed as a secondary endpoint using oil red O staining (for lipid content—see above), Movat's pentachrome staining (for lesion complexity including extracellular matrix and glycosaminoglycans), and haematoxylin and eosin (for macrophage content). The average atherosclerotic area is compared between the groups using the two-way ANOVA test. Additional secondary endpoints will be plasma levels of total cholesterol, HDL cholesterol, LDL cholesterol, triglycerides, and glucose, as well as en face visualization of the thoracic and abdominal aortas stained with oil red O.

It is expected that low-dose mycophenolate mofetil in the LDLRKO mice will attenuate atherosclerosis through suppression of the T-cell mediated arm of the inflammatory response. It expected that the size, composition and/or maturity of the lesions will be reduced by the drug. Measures of outcome that should improve include, but are not limited to, maturity of the lesion (as judged by histological analysis by a qualified cardiovascular pathologist, blinded to treatment), reduction in the percentage of the aortic sinus occluded by atheroma from 21.1+/−4.5% to 16.6+/−4.5%, reduction in the amount of degenerative tissue present within the lesion, and reduction in lesion complexity. A decrease in lesion maturity is also expected, indicative of an attenuation in the initiation of the atheromatous process ("younger lesions"). Also expected is a reduction in serum and tissue inflammatory mediators, such as, but not limited to, CRF, VCAM-1, ICAM-1 and matrix metalloproteases.

Results of administering low dose MMF: FIG. 1 shows the effect of mycophenolate mofetil given at a dosage of 15 mg/kg/day in reducing atherosclerosis (AS), as assessed by percentage of aortic sinus occluded by plaque, in male Ldlr−/− mice. Low-dose therapy (15 mg/kg/day, a dosage equivalent to approximately 1 gram per day in a 70 kg human) reduced AS by 31% (from 16% to 11% of the sinus) whereas high-dose therapy reduced AS by 61% (from 16% to 6.2%). The response was dose-dependent. Quantification was performed by a single, trained observer blinded to treatment group.

Figure 2:
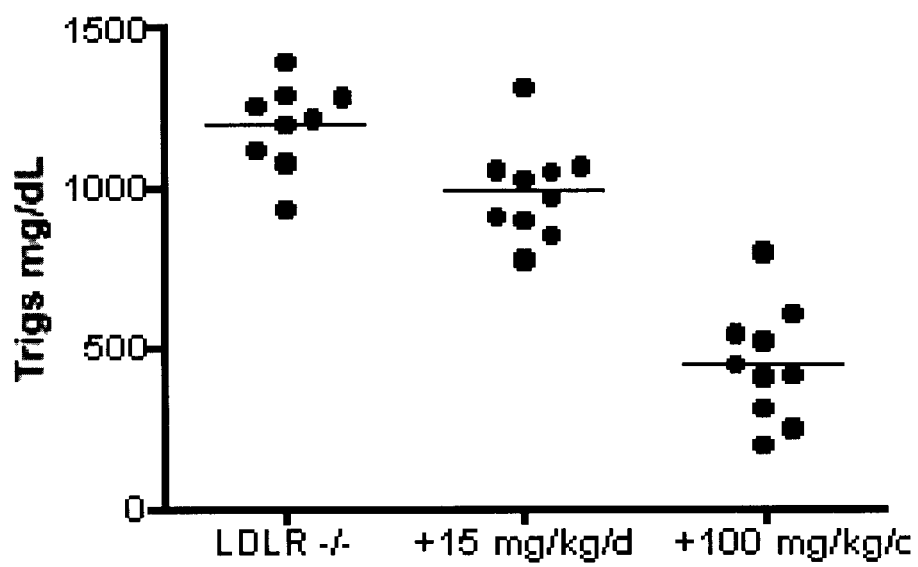
FIG. 2 illustrates the effect of mycophenolate mofetil in reducing serum triglycerides (Tgs) in male Ldlr–/– mice when given at a dosage of 15 mg/kg/day.

FIG. 2 shows the effect of mycophenolate mofetil given at a dosage of 15 mg/kg/day in reducing serum triglyceride (Tgs) levels in male Ldlr−/− mice. Low-dose therapy reduced Tgs from 1198+137 mg/dL to 994+149 mg/dL whereas high-dose therapy reduced Tgs to 452+80 mg/dL. The response was dose-dependent. Quantification was performed by a single, trained observer blinded to treatment group. Mouse groups are the same as for FIG. 1.

Figure 3:
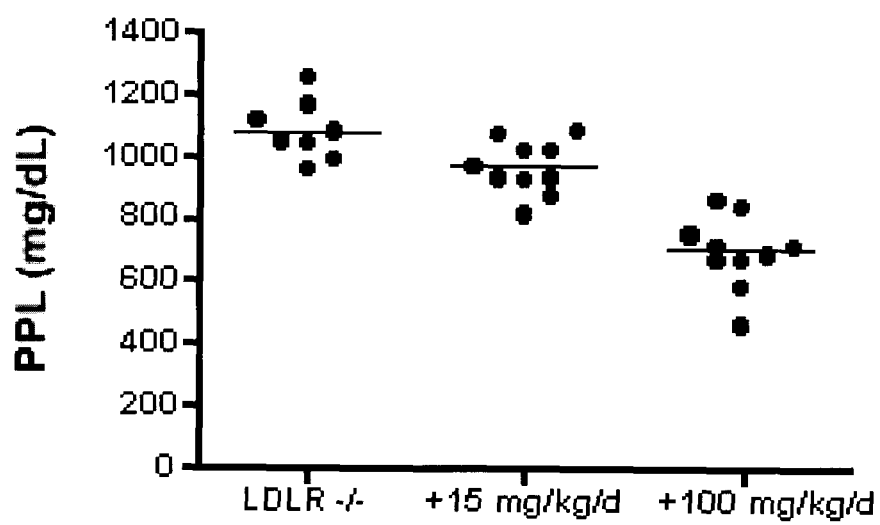
FIG. 3 illustrates the effect of mycophenolate mofetil in reducing serum phospholipids (PPL) in male Ldlr–/– mice when given at a dosage of 15 mg/kg/day.

FIG. 3 shows the effect of mycophenolate mofetil given at a dosage of 15 mg/kg/day on serum phospholipid (PPL) levels in male Ldlr−/− mice. Low-dose therapy reduced PPL from 1078+91 mg/dL to 964+87 mg/dL whereas high-dose therapy reduced PPL to 696+115 mg/dL. The response was dose-dependent. Quantification was performed by a single, trained observer blinded to treatment group. Mouse groups are the same as for FIG. 1.

Figure 4:
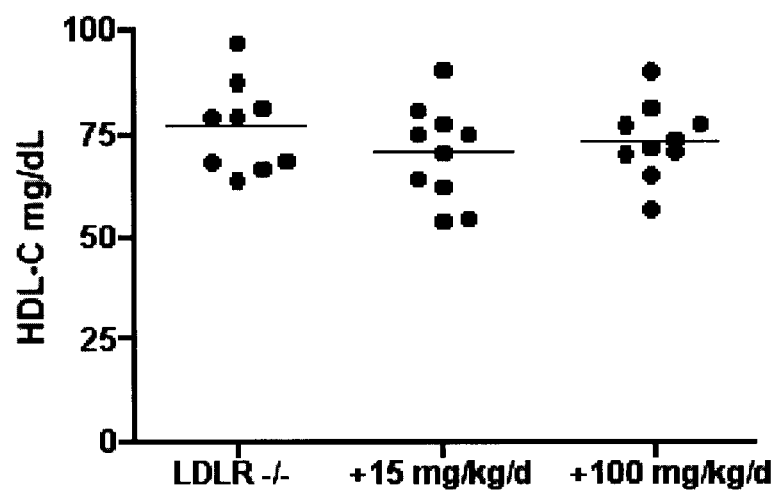
FIG. 4 illustrates the effect of mycophenolate mofetil on high-density lipoprotein levels in male Ldlr–/– mice when given at a dosage of 15 mg/kg/day.

FIG. 4 shows that mycophenolate mofetil does not appear to affect HDL levels, thus indicating that MMF reduces atherosclerosis through mechanisms independent of raising high-density lipoprotein. Importantly, levels of serum HDL-cholesterol are not lowered by MMF treatment. Quantification was performed by a single, trained observer blinded to treatment group. Mouse groups are the same as for FIG. 1.

Figure 5:
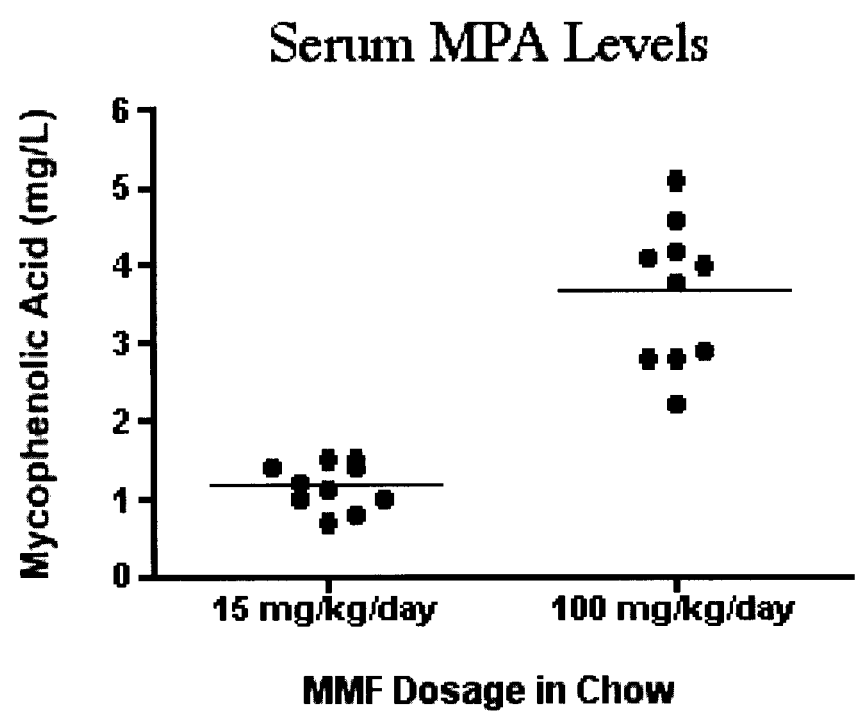
FIG. 5 illustrates the serum levels of mycophenolate mofetil in Ldlr–/– mice for corresponding dosages of 15 mg/kg/day and 100 mg/kg/day.

FIG. 5 shows Data Quality Assurance in which serum mycophenolic acid (MPA) levels were measured by commercial assay at the Vancouver General Hospital Special Chemistry laboratory. No MPA was detected in the serum of control mice (data not shown). The average serum level in the low-dose group was 1.16+0.09 mg/L, and in the high-dose group 3.65+0.3 mg/L, indicating that the drug remained stable and active after incorporation into the high-fat mouse chow.

Example 2

Effect of Low Dose MMF in a High-Cholesterol Rabbit Model

This example illustrates the use of low dose MMF in the treatment of a rabbit model of atherogenesis.

Study Design: Studies are done in 30 male New Zealand White (NZW) rabbits weighing 1.0-1.5 kg at the beginning of the experiment. After obtaining baseline blood samples, rabbits are fed ad libitum a 1% cholesterol diet for 12 weeks. This diet is prepared by dissolving cholesterol (Sigma, St. Louis, Mo.) in 100% ethanol at a temperature of 60° C., mixing this solution with standard rabbit chow (Purina), and allowing the complete evaporation of the ethanol.

The rabbits are divided into three groups and treated as follows: (1) CHOL+MMF (extra-low) group (n=10) receives by gastric gavage 5 mg/kg of MMF in 0.4 ml of water; (2) CHOL+MMF (ultra-low) group (n=10) receives by gastric gavage 1 mg/kg of MMF in 0.4 ml of water; and (3) CHOL group (n=10) receives by the same route daily 0.4 ml of water. Since the MMF is insoluble in water, the drug is individually prepared as a suspension by vigorous shaking immediately before administration. The MMF and vehicle are given daily throughout the 12 experimental weeks.

Blood samples for determination of plasma cholesterol and triglyceride are taken every 2 weeks.

A separate set of rabbits of similar weight is kept for 12 weeks on a standard rabbit chow not supplemented with cholesterol and sacrificed to determine normal values.

Animals are sacrificed at the end of the 12$^{th}$ week. The aorta is rapidly dissected and cut from the beginning of the aortic arch to the bifurcation of the iliac vessels. Then, thoracic and abdominal segments of the aorta are separated using the diaphragm as a reference point. Aortic rings of about 1 mm width are cut at the initiation of the aortic arch for histologic and immunohistologic analysis. Then, thoracic and abdominal segments of the aorta are opened longitudinally and photographed for evaluation of the extension of atherosclerotic plaques. The adventitia is then carefully separated and the aortic segments are weighed and used for determination of the total cholesterol content.

Determination of aortic cholesterol content: Lipids are isolated from the aortic segments as described by Folch et al., 1957, *J Biol Chem.* 266:497-509. Briefly, tissue is homogenized in a mixture of chlorophorm-methanol 2:1 (v:v) in a final volume 20 times the mixture volume. Homogenates are centrifuged at 2500 rpm for 15 min, and the supernatant is washed in ionic 0.017% $MgCl_2$ solution and then centrifuged for 20 min. Lipids are extracted from the lower layer. Cholesterol is determined in the lipid extract by the method of Zlatikis et al., 1953, *J Lab Clin Med.* 1:486-492.

Expected Results: The size and severity of the atherosclerotic lesion, as measured by the intima/media ratio, and by aortic cholesterol content, is expected to be significantly reduced in the MMF-treated rabbits. Size and severity of atherosclerotic lesions in rabbits of the ultra-low (1 mg/kg) group are expected to be similar to those of the extra-low (5 mg/kg) group.

Example 3

Effect of Low-Dose MMF on a Mouse Model of SLE

Study Design: This example illustrates the effect of low-dose MMF on the mouse model of the W/B F1 cross (New Zealand White×BXSB F1), recognized as the closest model to the human disease SLE. W/B F1 mice are bred according to previous protocols (Hang et al., 1981, *J Exp Med.* 154:216-221) and obtained from Jackson Labs. Eighty percent of W/B F1 males are expected to develop a degenerative vascular disease confined predominantly to the coronary artery system, which is often associated with myocardial infarction.

Male W/B F1 mice are divided in three groups and treated as indicated: (1) MMF (extra-low) group (n=10) receives by gastric gavage 5 mg/kg of MMF in 0.1 ml of water; (2) MMF (ultra-low) group (n=10) receives by gastric gavage 1 mg/kg of MMF in 0.1 ml of water; and (3) control group (n=10), which receives by the same route 0.1 ml water daily. Since the MMF is insoluble in water, the drug is individually prepared as a suspension by vigorous shaking immediately before administration. The MMF and vehicle are given daily throughout the 20 experimental weeks.

Survival of control animals is approximately 50% at the end of 20 weeks. At the end of 20 weeks of treatment MMF treated animals are expected to demonstrate improved survival and reduced evidence of disease.

Example 4

A Multi-Center, Open-Label, Placebo-Controlled Study Evaluating the Effects of Low-Dose Mycophenolate Mofetil on Atherosclerosis in Patients Undergoing Cartotid Endarterectomy Study Design: This study will consist of two phases. In phase I, two groups of 10 patients each will be included. After phase I, an interim analysis will be performed, and based on the results from the interim analysis, the power calculation for phase II will be recalculated. It is anticipated that 15 patients will be added to both groups in phase II which would bring the total to 25 patients in the MMF and 25 patients in the placebo treated group.

In total, 50 patients will be included at the Departments of Neurology and Vascular Surgery of the Academical Medical Center (Amsterdam), the Utrecht Medical Center (Utrecht), and St Antonius Ziekenhuis (Nieuwegein).

After randomization, the second and final visit is scheduled. Patients will be treated for a minimum of three weeks and for a maximum of 12 weeks, and the second visit is planned allowing a washout period of 12 hours prior to surgery. During this second visit, all measurements of Visit 1 will be repeated. Subsequently, study medication will be discontinued. At time of surgery, endarterectomy specimens will be collected for immunostaining to establish the effects of T-cell inhibition on atherosclerotic plaque composition.

Study Population (Inclusion Criteria): Eligibility will be evaluated on the basis of available clinical data from the last outpatient clinic visit. Consecutive patients with >70% diameter carotid artery stenosis (as assessed by angiography or ultrasonography) who also have ipsilateral transient ischemic attack (TIA) and who are planned to undergo carotid endarterectomy (CEA) will be included and treated for a minimum of three weeks prior to surgery. If patients are eligible for the study, informed consent will be asked by the treating physician. If consented, the patients are invited for the first study visit. During this visit, they will be randomized to either placebo or MMF treatment.

Study Population (Exclusion Criteria): Patients who are unable to tolerate MMF treatment, who withdraw their consent, or those with any other medical condition or laboratory abnormality, which in the opinion of the principal investigator could affect subject safety, preclude evaluation of response, or render unlikely that the patient would complete the study, will be excluded.

Study Protocol: At Visit 1, information regarding baseline characteristics, use of medication and clinical data will be acquired. In addition biochemical markers will be determined (i.e., hemoglobin, platelets, leukocyte differentiation, (hs) CRP, leverenzymes, HDL- and LDL-cholesterol and triglycerides). In total 50 ml blood will be withdrawn of which the remainder will be frozen for additional analysis. Subsequently, patients will receive study medication.

Study Drug: Mycophenolate Mofetil (Cellcept®) will be given at a dose of 1000 mg BD. To avoid gastrointestinal side effects, the dose will be initiated at 500 mg BD for a period of 3-7 days. After the first week, patients will increase their dosage to 1000 mg BD. Patients will be treated for a minimum of three weeks.

Preliminary Data and Power Calculation: Carotid endarterectomy specimens of 9 patients were analyzed for presence and activation status of T-lymphocytes (see Table I).

TABLE I

Percentage of T-lymphocytes and their activation status in 9 CEA specimens

| Patient | % CD4/CD3 | % CD40L/CD3 |
|---|---|---|
| 1 | 70.5 | 16.2 |
| 2 | 57.2 | 3.7 |
| 3 | 69.3 | 10.2 |
| 4 | 46.8 | 55.7 |
| 5 | 71.9 | 26.0 |
| 6 | 104.0 | 24.4 |
| 7 | 69.1 | 50.9 |
| 8 | 106.9 | 48.9 |
| 9 | 90.2 | 21.9 |
| mu | 76.2 | 28.7 |
| delta | 20.3 | 18.8 |

Based on these historical controls, a sample size of 25 in each group will have 80% power to detect a difference in means of 16.2 (the difference in mean % CD4/CD3 ratio between placebo of 76.2 and MMF group of 60) assuming that the common standard deviation is 20.0 using a two group t-test with a two-sided significance level of 0.050. A sample size of 25 in each group will also have 80% power to detect a difference in means of 15.4 (the difference in mean % CD40L/CD3 between placebo of 29.0 and MMF group of 13.6) assuming that the common standard deviation is 19.0 using a two group t-test with a two-sided significance level of 0.050.

These calculated reductions are exceeded by the changes seen in atherosclerotic plaque phenotype following pravastatin therapy, wherein treatment reduced the percentage of CD3 positive cells from 24.3% to 11.2% (see, Crisby et al., 2001, "Pravastatin treatment increases collagen content and decreases lipid content, inflammation, metalloproteinases, and cell death in human carotid plaques: implications for plaque stabilization," *Circulation* 103:926-933). Although the duration of drug treatment planned is shorter than in the pravastatin treated cohort (i.e., 3 weeks MMF compared to 3 months of pravastatin), we expect to see similar or larger reductions in inflammatory status due to the more powerful immunosuppressive actions of MMF compared to statins.

The primary endpoint will be a decrease in the immunostaining of the endarterectomy specimens for the presence of T-cell surface markers such as CD3, CD4 and CD8. Markers of T-cell activation such as CD40L and CD69 will also be assessed. Real time PCR will be used to study the expression of markers for Th1 cells such as interferon-gamma, and for markers for Th2 cells such as IL-4. Immunostaining for CD86 will identify the presence of macrophages, which will be corroborated by real time PCR for macrophage markers such as IL-6.

Secondary endpoints will be the immunostaining of microcirculation and evaluating the expression of adhesion molecules VCAM-1, ICAM-1 and E-selectin, as well as CD31 to confirm the presence of endothelial cells. Immunostaining will also identify matrix metalloproteinases such as MMP and TIMP. Immunostaining will also be carried out for expression of tissue factor (CD142). Plaque composition will be assessed by caspase staining for cell death, oil red O staining for lipid content, and sirius red staining for smooth muscle cells and collagen.

Example 5

A Prospective, Randomized, Double-Blind, Placebo-Controlled Trial Evaluating The Effects Of Mycophenolate Mofetil (MMF) On Surrogate Markers for Atherosclerosis in Female Patients with Systemic Lupus Erythematosus (SLE)

These studies are based on the reasoning that MMF will attenuate inflammatory responses by reducing the production of pro-inflammatory cytokines, inhibiting T-cell number and activation, inhibiting adhesion molecule expression, decreasing the production of NO by inducible NOS as well as exerting direct anti-proliferative effects on numerous pro-atherogenic cell types. This is expected to be associated with a potent anti-inflammatory effect, which will translate into improvement of endothelial function and attenuation of the pro-inflammatory/oxidant parameters.

Study Design: This will be a double-blind, randomized, placebo-controlled trial evaluating the effects of mycophenolate mofetil on 'surrogate markers' for atherosclerosis in a group of female SLE patients. In total 100 patients will be selected from the database at St Thomas Hospital. Eligibility will be evaluated on the basis of available clinical data from the last outpatient clinic visit. If patients are eligible for the study, informed consent will be asked by the treating physician. If consented, the patients are invited for the first study visit.

At Visit 1, clinical data on baseline characteristics, SLE-DAI index, British Isles Lupus Assessment Group Index (BI-LAG), medications and biochemical markers will be collected and endothelial function will be determined (see below). Subsequently, patients will receive study medication. During Visit 1, they will be randomized to either placebo or MMF treatment. To avoid gastrointestinal side effects the dose will be initiated at 500 mg BID for a period of one week after which patients can double their dosage. Patients will be contacted by telephone 1 week after randomization. If the patient reports any adverse events, the patient may be requested (at the discretion of the investigator) to attend the clinic within 5 days for assessment.

Eight weeks after randomization, the second and final visit is scheduled. During this visit, all measurements of Visit 1 will be repeated. At Visit 1, patients will attend St. Thomas' Hospital before the FMD assessment at Great Ormond Street Hospital. At Visit 2, patients will have the FMD assessment before any other assessments. If the patient has an active infection at Visit 2 then this visit will be postponed for up to 2 weeks. Subsequently, study medication will be discontinued.

Study Population: Inclusion criteria are female SLE patients aged 18-50 years (premenopausal) with clinically stable disease and who are using a reliable method of contraception, taking hydroxychloroquine, and taking up to 15 mg of prednisolone daily. In total, 100 patients will be included divided equally over the two groups. The protocol will continue until at least 40 patients have completed both arms of the protocol.

Exclusion criteria are those who are smokers, pregnant or breast feeding, or using other immunosuppressants (apart from hydroxychloroquine and a stable dose of prednisolone, as outlined above). Similarly, the use of any other investigational drug within 1 month prior to screening, the presence of acute infections in the 2 weeks prior to Visit 1, and a history of ischemic heart disease, end stage renal disease, or current signs or symptoms of severe, progressive or uncontrolled hepatic, haematological, gastroenterological, endocrine, pulmonary, cardiac or neurological disease, will render a candidate ineligible for the study protocol.

Randomization Protocol: Patient allocation to treatment or placebo group will be performed using a minimization protocol. This method reduces differences between the groups, not only in the number of patients but in patient characteristics. The minimization criteria will be age, hypertension, dyslipidemia, renal impairment, diabetes mellitus and antiphospholipid antibody status.

Study Drug and Monitoring: Mycophenolate mofetil (Cellcept®) will be given at a dosage of 1000 mg BID. To avoid gastrointestinal side effects, the dose will be initiated at 500 mg BID for a period of one week, after which patients can double their dosage to 1000 mg BID. Study drug will be dispensed through the hospital pharmacy and full accountability logs kept. All patients will have a hematology panel taken weekly for the first month and every two weeks for the second month to monitor for excessive immunosuppression.

Study Measurements: Arterial Stiffness will be measured using the Ankle-Brachial Index, and also by Pulse Wave Analysis (see below). Endothelial function will be assessed using flow-mediated dilation as well as by GTN mediated dilation (see below).

Clinical parameters incorporated in the assessment will include the SLE Disease Activity Index (SLEDAI), body mass index, and blood pressure. In addition, lupus serological markers will be measured. These will include anti-DNA antibodies, complement levels, antiphospholipid antibodies, ESR, C-reactive protein, urine protein:creatinine ratio, hematology panel with differential count, and renal and liver function tests (LDH, AST and ALT). Specific biochemical parameters to be studied will include a standard lipid profile (total cholesterol, HDL cholesterol, LDL cholesterol and triglycerides). Nonstandard lipid profiling will include measures of apoAI, apoB and apoM, as well as HDL-quality (SAA, PON) and oxidized LDL. Fasting plasma glucose, BSE, hsCRP and sPLA2 will be collected, as will urinary isoprostane F2-alpha. Coagulation panel will include D-dimers, and F1+2 fragments. Additional non-standard inflammatory markers to be measured include IL-6, sCD40L, and MCP-1.

Methodology for Ankle-Brachial Index (ABI) Assessment: ABI will be measured using an 8 MHz Doppler ultrasound probe (mod MD200) and a 12 cm cuff attached to a mercury sphygmomanometer, which is applied to both arms and ankles. The Doppler probe is used to determine systolic blood pressure in both brachial arteries in the antecubital fossa, and in both posterior tibial and dorsalis pedis arteries. The cuff is inflated to 20 mm Hg above systolic arterial pressure and then slowly deflated. With the Doppler probe a systolic pressure is obtained when the Doppler signal is first heard. The ABI for each leg is calculated as the ratio of the higher of the two systolic arterial pressures (posterior tibial and dorsalis pedis) in the leg and the higher systolic pressure of either the left or right arm. The method used is in accordance with a recent consensus statement on measuring the ABI. An ABI<1.00 in either leg is considered abnormal, suggesting peripheral vascular disease; progressively lower ABI values indicate more severe obstruction.

Methodology for Pulse Wave Analysis (PWA): This measurement requires a pressure wave tonometer (fine pencil probe) attached to a sphygmocor pulse wave velocity recording machine. Pulse wave analysis is performed on supine fasted patients, with a blood pressure cuff on the left arm and a pressure transducer on the right radial artery. Age, gender, height and weight are entered before automated measurements of the heart rate, systolic and diastolic blood pressure and assessment of the pulse wave form at the radial artery are made. After data acquisition, the inbuilt software analyzes the wave form based on a modified Windkessel model of the circulation to calculate arterial elasticity and systemic vascular resistance. Data calculated also includes body mass index, pulse pressure, small artery elasticity (SAE), large artery elasticity (LAE) and systemic vascular resistance. The mean of three one-minute readings taken over 15 minutes is used. Reproducibility of the SAE and LAE are 9.8% and 10.2% respectively.

Methodology for Endothelium Dependant and Endothelium Independent Dilatation: This is carried out using a high resolution ultrasound machine with vascular and cardiac capabilities, a high frequency (5-13 mHz) linear array probe, a super VHS video and printer, and an arm rest with stereo tactic clamp. Computer image acquisition and analysis software for diameter measurements is also required. These studies will be carried out in a warm temperature-controlled room. The patients should ideally be fasting or have had only a low fat meal and intake of caffeine should be curtailed for at least 2 hours prior to the study. Cardiovascular risk factors, e.g., diabetes, hypertension, smoking, family history, medications and recent/current infections will be documented, along with the stage of menstrual cycle in women. The patient is asked to rest in a supine position for at least 10 mins (for blood pressure stabilization). Three monitoring ECG electrodes are attached to the chest. The brachial artery is imaged in longitudinal section, 5-10 cms proximal to placement of a blood pressure cuff, just below the ante cubital fossa. It has been shown that the dilatation using this cuff/probe position can be blocked by infusion of LNMMA into the forearm and is therefore nitric oxide dependent. The probe is held in a stereo tactic clamp, with micrometer movement capabilities for fine adjustment. When the clearest B-mode image through the centre of the vessel is obtained with optimal contrast between the anterior and posterior vessel walls and the lumen of the vessel, the stereo tactic clamp is fixed in place. A Doppler signal is recorded from the centre of the vessel with the range gate set at 1.5 mm. The B-mode is set to update synchronous with the R-Wave of the ECG whilst also having a continuous Doppler spectrum recording throughout.

Methodology for Endothelium-Dependent (Flow-Mediated) Dilation: The baseline image and Doppler signal will be recorded for 1 min, following which the blood pressure cuff will be inflated to suprasystolic pressure for 5 mins. The cuff will then be rapidly deflated and the artery imaged and Doppler signal recorded for 5 mins post-cuff deflation. Brachial artery FMD is calculated as the maximum change in diameter from baseline, expressed as a percentage change. Upon cuff deflation, the resultant reactive hyperaemia is calculated as the flow change from baseline, expressed as a percentage change in blood flow. It is accepted that errors are inherent in the flow velocity measures at a Doppler angle of 70 degrees in the centre of the vessel but relative changes are accurate.

Methodology for Endothelium-independent (GTN mediated) Dilatation: In contrast, the effect of an endothelium independent stimulation can be assessed by administration of a sublingual dose of GTN. As with assessment of FMD, the baseline image and Doppler signal will be recorded for 1 min. GTN is then administered sublingually, and the image and Doppler signal are recorded for a further 5 mins. GTN-mediated brachial artery dilatation is calculated as the maximum change from baseline, expressed as a percentage change in diameter.

Statistical Considerations and Analysis Plan—Power Calculations: In a recent study the number of subjects assessed by El-Magadmi et al. (38 unaffected controls and 62 SLE patients) should have been sufficient to observe a FMD difference of approximately 3.3% (see, El-Magadmi et al., 2004, "Systemic lupus erythematosus: an independent risk factor for endothelial dysfunction in women," *Circulation* 110(4): 399-404). The difference between case mean and control mean is 3.3% as observed (assuming a Gaussian distribution of FMD's). The Standard Deviation (SD) reported by Lima et al. was 5, the number of control/case ratio being 0.61 (=38/62), alpha=0.05; beta 0.2 (Lima et al. 2001, "Brachial endothelial function is impaired in patients with systemic lupus erythematosus." *J Rheumatol* 29:292-297). With the assumed difference of 3.3% (a conservative estimate) and if the SD of the means of the paired repeated differences is 3.9% (as per the DALM abstract—data on file with Aspreva) the number of SLE subjects would be approximately 41; however with a beta of 0.1 (power 90%), the patient numbers need to increase to account for the control ratio in the El-Magadmi study from 1:0.6 to 1:1. This would allow a detection of a difference of 3.3% in a patient population of 31 SLE and 31 controls.

Data Quality Assurance: Data for all assessment other than the FMD and GTN dilation will be recorded on paper case report forms (CRFs). The data for FMD and GTN dilation will be recorded electronically. Accurate and reliable date collection will be assured by verification and cross-check of 100% of CRFs against the investigator records (source documents) by a study monitor. All date will be entered into a computer database and subject to quality assurance.

Safety Issues, Including Adverse Events and Laboratory Abnormalities: An adverse event (AE) is any untoward medical occurrence in a clinical investigation subject. An AE can therefore be any unfavorable and unintended sign, symptom, or disease temporally associated with the use of a pharmaceutical product (including placebo and comparative agents), whether or not considered related to the pharmaceutical product. Pre-existing conditions that worsen during a study are to be reported as AEs. Such adverse events will be graded on a three-point scale (i.e., mild, moderate or severe) and reported in detail as indicated on the CRF. A "mild" AE will consist of discomfort that does not disrupt normal activity. A "moderate" AE will consist of discomfort sufficient to reduce or affect normal daily activity, and an AE will be considered "severe" if it causes the inability to work or perform normal daily activities.

The date of onset and cessation of each AE, any intervention initiated by the investigator, and the outcome will be recorded. Adverse events persisting at the time of study completion will be followed by the investigator through contact with the subject until a clinically acceptable resolution or stabilization has occurred, or until the event is progressing according to the expected clinical course. If the subject reports an AE, it will be the investigator's responsibility to acquire sufficient information in order to assess causality. This may require additional laboratory testing, physical examinations, telephone contacts, etc. The relationship of the adverse event to the treatment will be assessed.

Laboratory Test Abnormalities: Laboratory test results will be recorded on the laboratory results pages of the CRF, or appear on electronically produced laboratory reports submitted directly from the central laboratory. Laboratory test value abnormalities as such will not be reported on the AE page of the CRF as AEs unless they are considered clinically significant by the investigator. In the event of unexplained abnormal laboratory test values, the tests will be repeated immediately and followed up until they have returned to the normal range and/or an adequate explanation of the abnormality is found. If a clear explanation is established, it will be recorded on the CRF.

Handling of Safety Parameters: The sponsors of the study, Guy's and St Thomas' Trust, will be responsible for pharmacovigilance, and any serious adverse events occurring during the study will be reported to the Trust. A serious adverse event (SAE) is any experience that suggests a significant hazard, contraindication, side-effect or precaution. With respect to human clinical experience, this includes any experience that results in persistent or significant disability/incapacity, requires in-patient hospitalization or prolongation of existing hospitalization, is life-threatening or results in death. Congenital anomalies or birth defects arising in the offspring of women who become pregnant during the study (see below) will also be recorded as SAEs, though causality in such cases will admittedly be difficult to establish.

Medical and scientific judgment will be exercised in deciding whether expedited reporting is appropriate in other situations, such as important medical events that may not be immediately life-threatening or result in hospitalization or death, but may jeopardize the subject or may require intervention to prevent one of the other outcomes listed in the definition above. These will also usually be considered serious. Examples of such events are intensive treatment in an emergency room or at home for allergic bronchospasm; blood dyscrasias or convulsions that do not result in hospitalization; or development of drug dependency or drug abuse.

The term "severe" is a measure of intensity: thus a severe adverse event is not necessarily serious. For example, nausea of several hours' duration may be rated as severe, but may not be clinically serious. The death of a study participant which comes to the attention of the investigator during the study or within 4 weeks after stopping the treatment (whether considered treatment-related or not), will be reported to the Trust. Preliminary reports will be followed by detailed descriptions which will include copies of hospital case reports, autopsy reports and other documents when requested and applicable.

For all SAEs, the following will be assessed and recorded on the AE page of the CRF: intensity, relationship to test substance, action taken regarding test substance, and outcome to date. The investigator will notify the IRB and/or IEC of such an event in writing as soon as is practical, and in accordance with international and local laws and regulations.

Pregnancy: Study subjects will be instructed to stop taking study medication and immediately inform the investigator if they become pregnant during the study. The Medical Monitor will then be contacted immediately to break the blind. The investigator will counsel the subject and discuss the risks of continuing with the pregnancy and the possible effects on the fetus. Monitoring of the subject will continue until conclusion of the pregnancy. Pregnancies occurring up to 90 days after the completion of the study medication that come to the attention of the investigator will also be reported to the sponsor. Pregnancies will be formally reported as AEs to ensure full documentation.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating atherosclerosis associated with a vascular, autoimmune and/or inflammatory disease, comprising administering to a human subject in need thereof an effective amount of mycophenolate mofetil (MMF), wherein the amount administered is less than 0.5 g/day.

2. The method of claim 1 in which the disease is a vascular disease.

3. The method of claim 1 in which the disease is an autoimmune disease.

4. The method of claim 3 in which the autoimmune disease is systemic lupus erythematosus (SLE), multiple sclerosis (MS), diabetes mellitus, or rheumatoid arthritis (RA).

5. The method of claim 1 in which the MMF is administered orally.

6. The method of claim 5 in which the MMF is administered once per day.

7. The method of claim 5 in which the MMF is administered twice per day.

8. The method of claim 1 in which the amount of MMF administered is about 0.05 to 2 mg/kg body weight/day.

9. The method of claim 8 in which the amount of MMF administered is about 0.05 to 0.30 mg/kg body weight/day.

10. The method of claim 8 in which the amount of MMF administered is about 0.05 to 0.50 mg/kg body weight/day.

11. The method of claim 8 in which the amount of MMF administered is about 0.05 to 0.90 mg/kg body weight/day.

12. The method of claim 8 in which the amount of MMF administered is about 0.05 to 1.50 mg/kg body weight/day.

13. The method of claim 1 in which the amount of MMF administered is about 1 to 4 mg/kg body weight/day.

14. The method of claim 13 in which the amount of MMF administered is about 1 to 2 mg/kg body weight/day.

15. The method of claim 13 in which the amount of MMF administered is about 1 to 3 mg/kg body weight/day.

16. The method of claim 1 in which the amount of MMF administered is 5 to 100 mg/day.

17. The method of claim 1 in which the amount of MMF administered is about 100, 125, 150, 175, 200, 225, 250, 300, 350, or 400 mg/day.

18. The method of claim 1 in which the amount of MMF administered is about 5, 10, 20, 25, 30, 40, 50, 60, 70, 75, 80, 90, or 100 mg/day.

* * * * *